United States Patent
Zapalac

(10) Patent No.: US 6,842,499 B2
(45) Date of Patent: Jan. 11, 2005

(54) METHOD AND APPARATUS FOR CONNECTING TEMPORALLY SEPARATED SINOGRAMS IN AN EBT SCANNER

(75) Inventor: Geordie Henry Zapalac, Grass Valley, CA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/065,757

(22) Filed: Nov. 15, 2002

(65) Prior Publication Data

US 2004/0096027 A1 May 20, 2004

(51) Int. Cl.[7] .............................................. G01N 23/00
(52) U.S. Cl. .............................. 378/12; 378/4; 378/901
(58) Field of Search .............................. 378/12, 13, 14, 378/4, 21, 901; 382/131

(56) References Cited

U.S. PATENT DOCUMENTS

| 4,352,021 A | 9/1982 | Boyd et al. |
|---|---|---|
| 4,521,900 A | 6/1985 | Rand |
| 4,521,901 A | 6/1985 | Rand |
| 4,625,150 A | 11/1986 | Rand |
| 4,644,168 A | 2/1987 | Rand et al. |
| 5,193,105 A | 3/1993 | Rand et al. |
| 5,289,519 A | 2/1994 | Rand et al. |
| 5,406,479 A * | 4/1995 | Harman .......................... 378/7 |
| 5,719,914 A | 2/1998 | Rand et al. |
| 6,208,711 B1 | 3/2001 | Rand et al. |

* cited by examiner

*Primary Examiner*—David V. Bruce
*Assistant Examiner*—Hoon Song
(74) *Attorney, Agent, or Firm*—McAndrews, Held & Malloy, Ltd.; Peter J. Vogel; Michael A. Dellapenna

(57) ABSTRACT

A method and apparatus are disclosed in an EBT scanner for generating an image from a data set collected from a subject beginning at an arbitrary time within a scanning time interval. A sequence of temporally separated, unfolded parallel view sinograms are generated corresponding to scans through the subject during the scanning time interval. Data from each of the sinograms are folded into each other such that loss of information and image artifacts, caused by temporal separation between temporally adjacent sinograms, are greatly reduced. An image is generated from a subset of data taken from the folded sinograms wherein the subset of data begins at an arbitrary time within the scanning time interval.

22 Claims, 7 Drawing Sheets

METHOD AND APPARATUS FOR CONNECTING TEMPORALLY SEPARATED SINOGRAMS IN AN EBT SCANNER

BACKGROUND OF INVENTION

Certain embodiments of the present invention relate to an electron beam tomography (EBT) scanner. More particularly, certain embodiments relate to a method and apparatus for generating an image from a data set collected from a subject beginning at an arbitrary time within a scanning time interval.

EBT scanners are generally described in U.S. Pat. No. 4,352,021 to Boyd, et al. (Sep. 28, 1982), and U.S. Pat. No. 4,521,900 (Jun. 4, 1985), U.S. Pat. No. 4,521,901 (Jun. 4, 1985), U.S. Pat. No. 4,625,150 (Nov. 25, 1986), U.S. Pat. No. 4,644,168 (Feb. 17, 1987), U.S. Pat. No. 5,193,105 (Mar. 9, 1993), U.S. Pat. No. 5,289,519 (Feb. 22, 1994), U.S. Pat. No. 5,719,914 (Feb. 17, 1998) and U.S. Pat. No. 6,208,711 all to Rand, et al., and U.S. Pat. No. 5,406,479 to Harman (Apr. 11, 1995). Applicants refer to and incorporate herein by reference each above listed patent to Rand, et al. and Harman.

As described in the above-referenced Rand et al. patents, an electron beam is produced by an electron gun at the upstream end of an evacuated, generally conical shaped housing chamber. A large negative potential (e.g. 130 kV or 140 kV) on the electron gun cathode accelerates the electron beam downstream along the chamber axis. Further downstream, a beam optical system that includes solenoid, quadrupole, and deflection coils focus and deflect the beam to scan along an X-ray producing target. The final beam spot at the X-ray producing target is smaller than that produced at the electron gun, and must be suitably sharp and free of aberrations so as not to degrade definition in the image rendered by the scanner.

The X-rays produced by the target penetrate a patient or other object and are detected by an array of detectors. The detector array, like the target, is coaxial with and defines a plane orthogonal to the scanner axis of symmetry. The output from the detector array is digitized, stored, and computer processed to produce a reconstructed X-ray video image of a slice of the object, typically an image of a patient's anatomy such as the heart or lungs.

An EBT scanner allows for the collection of many angles of view and scanning of a number of slices in a short time. There is no mechanically moving gantry. Both high resolution and dynamic scanning modes may be provided while eliminating the need for any target or detector motion by replacing conventional X-ray tubes with electron beam technology.

Multiple views may be generated by magnetically steering a focused electron beam along a 210 degree target ring positioned beneath a subject. Opposite the target ring is a stationary detector ring of Cadmium tungstate crystals encompassing a 216 degree arc above the subject. Photodiodes in the detector ring are used for recording transmitted X-ray intensity.

Each scan of a target ring requires 52 milliseconds followed by a 6 millisecond reset time before starting the next scan. The high-speed capability of the EBT scanner offers significant advantage over the gated conventional CT method and images over much of the entire apex-to-base extent of the heart or lungs may be obtained. Since movement by the heart and lungs may degrade image quality, it is extremely important to complete a scan in a limited amount of time. EBT technology allows for the high-speed scanning that is required.

CT scanners that do not use electron beam technology typically scan and collect data over a full 360 degrees. Data is taken continuously during a spiral scan and the data used to generate an image may be selected to begin at any point during the scan. As a result, the image time is independent of when the scan was triggered which is of value, for example, when searching for nodules in the lungs.

For scanners using electron beam technology, it is not possible to collect the data over 360 degrees. A data set is instead collected over, typically, 210 degrees. During scanning, the electron beam crosses a beam stop for typically a 6 millisecond interval between scans. Therefore, data sets are temporally separated from each other by the 6 millisecond gap.

Currently, the temporally separated data sets are each separately reconstructed into an image. As a result, the time for each image slice is determined by the initial conditions at the beginning of the corresponding scan and may not be varied in a continuous manner. As a result, the temporal discontinuities between temporally adjacent scans may cause information to be missed or unwanted artifacts, such as streaks, to appear in an image when trying to reconstruct the image across a temporal boundary.

It is often desirable to construct images starting at arbitrary times within the scanning interval requiring imaging across scan slice (sinogram) temporal boundaries. Therefore, electron beam scanners are at a disadvantage, due to the temporal discontinuities, compared to conventional CT scanners.

For example, in EBT angiography, scans are taken repeatedly at the same z-position through the patient during each cardiac cycle. Also, if the table that the patient is laying on is moved at a constant velocity along the z-axis, then the desire to create an image at an arbitrary time during the scanning time interval is equivalent to creating an image at an arbitrary z-position. CVS (continuous volume scanning) attempts to center the image data about an arbitrary z position when searching for nodules in the lungs.

A need exists to compensate for image artifacts and loss of information due to temporal separation between temporally adjacent sinograms produced by an EBT scanner such that construction of quality images across sinogram temporal boundaries is achieved.

SUMMARY OF INVENTION

An embodiment of the present invention provides an approach for generating an image from a data set collected by scanning a subject with an EBT scanner beginning at an arbitrary time within a scanning time interval.

A method is provided for generating a sequence of temporally separated, unfolded parallel view sinogram data sets corresponding to temporally adjacent scanned slices through a subject during a scanning time interval. Data from a first region of view angles from each of the sinogram data sets is folded into a second region of view angles in a corresponding next temporally adjacent sinogram data set. Data from a third region of view angles from each of the sinogram data sets is folded into a fourth region of view angles in a corresponding previous temporally adjacent sinogram data set. An image is generated from a subset of data taken from the folded sinogram data sets wherein the subset of data begins at an arbitrary time within the scanning time interval.

Apparatus is also provided including a sinogram pre-processing module generating a sequence of temporally separated, unfolded parallel view sinogram data sets corresponding to scanned slices through a subject during a scanning time interval. A sinogram data folding module is also provided for folding data from a first region of view angles from each of the sinogram data sets into a second region of view angles in a corresponding next temporally adjacent sinogram data set, and the sinogram data folding module folds data from a third region of view angles from each of the sinogram data sets into a fourth region of view angles in a corresponding previous temporally adjacent sinogram data set. An image processing module is provided to generate image data from a subset of data taken from the folded sinogram data sets wherein a subset of data begins at an arbitrary time within the scanning time interval.

Certain embodiments of the present invention afford an approach to combine sinograms generated by an EBT scanner such that loss of information and image artifacts, caused by temporal separation between temporally adjacent sinograms, is greatly reduced when imaging across sinogram temporal boundaries.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION

Figure 1:
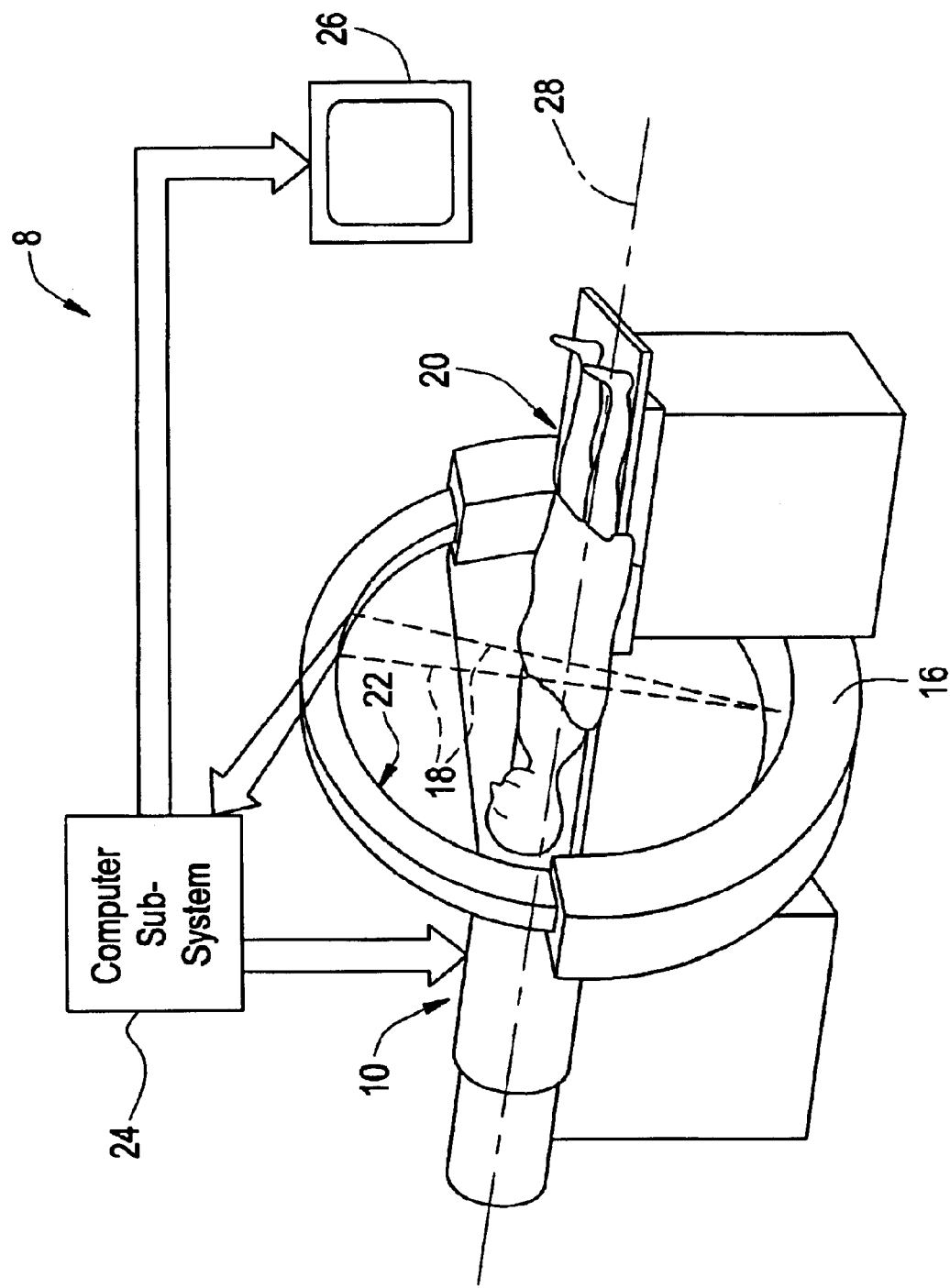
FIG. 1 is an illustration of a typical EBT scanner system that is used in accordance with an embodiment of the present invention.
Figure 2:
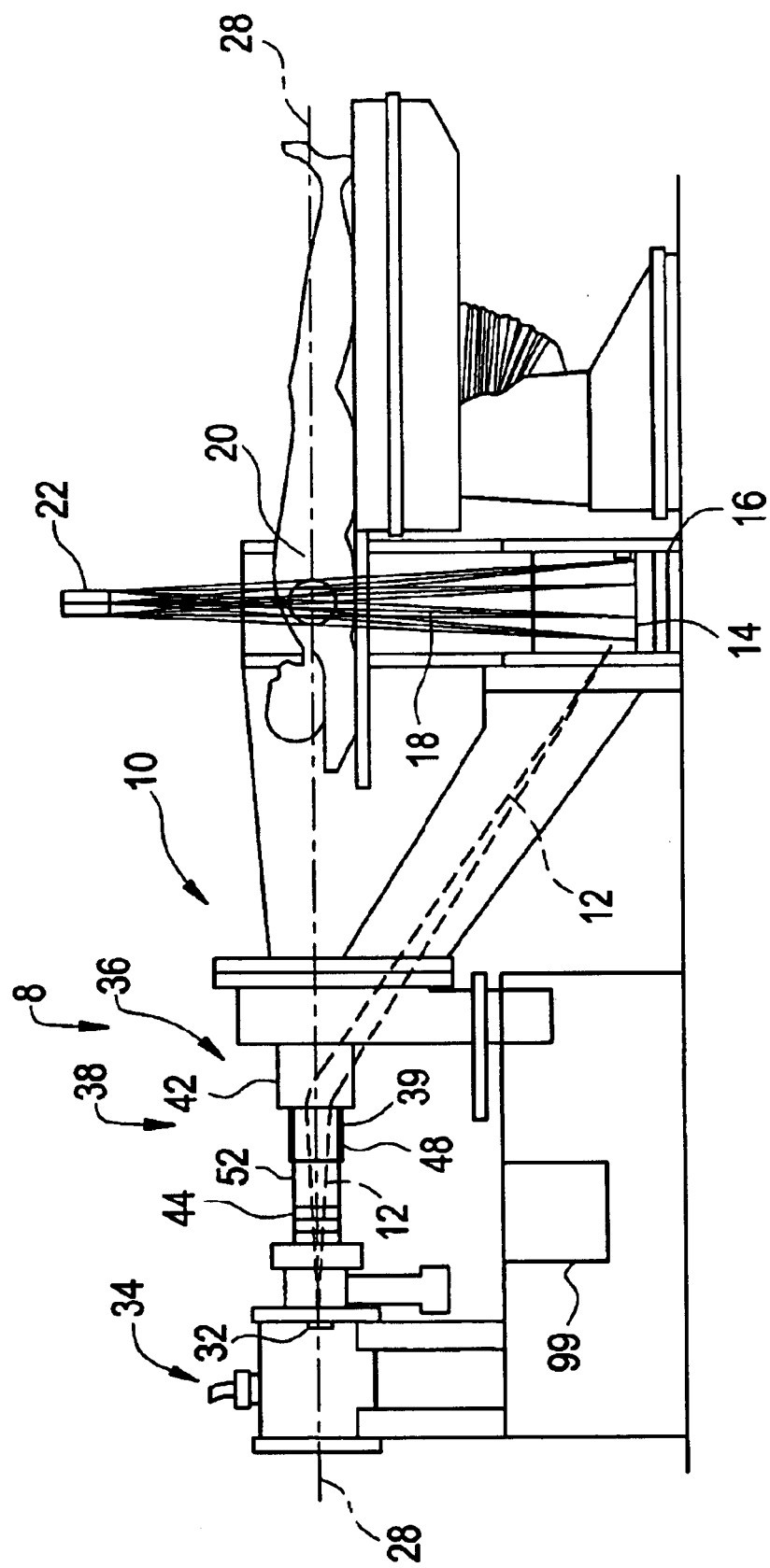
FIG. 2 is a more detailed illustration of the EBT scanner system of FIG. 1 showing how an electron beam and X-ray emission traverse through the system in accordance with an embodiment of the present invention.

Before describing certain embodiments of the present invention, it is helpful to understand the operation of an EBT scanner. FIG. 1 and FIG. 2 illustrate such a generalized system 8 according to certain embodiments of the present invention. System 8 includes a vacuum chamber housing 10 in which an electron beam 12 is generated at the cathode of an electron gun 32 located in upstream region 34, in response to perhaps 130 kV high voltage. The electron beam is then caused by optical system 38, including magnetic lens 39 and deflection coil 42, to scan at least one circular target 14 located within a front lower portion 16 of housing 10.

When scanned by the focused electron beam 12, the target 14 emits a moving fan-like beam of X-rays 18. X-rays 18 then pass through a region of a subject 20 (e.g. a patient or other object) and register upon a detector array 22 located diametrically opposite. Detector data is output to a computer subsystem 24 that processes and records the data, producing an image of a slice of the subject on a video monitor 26. The computer subsystem 24 also controls the system 8 and the electron beam production therein.

Beam optical system 38 is mounted within housing 10 and includes magnetic lens 39, deflecting coils and quadrupole coils (collectively coils 42), and an electrode assembly 44. Coils 39 and 42 contribute a focusing effect to help shape the final beam spot as it scans one of the targets 14.

Electrode assembly 44 is mounted within housing 10 between the electron gun 32 and the beam optical assembly 38 such that the electron beam 12 passes axially through assembly 44 along the Z-axis 28. Ideally, the Z-axis 28 is coaxial with the electron beam 12 upstream from the beam optics assembly 38 within chamber 10. Axis 28 also represents the longitudinal axis of chamber 10, and the axis of symmetry for the electrode assembly 44 and the beam optics assembly 38 in accordance with an embodiment of the present invention. The Z-axis 28 is also the scanning axis through a subject being scanned.

Figure 3:
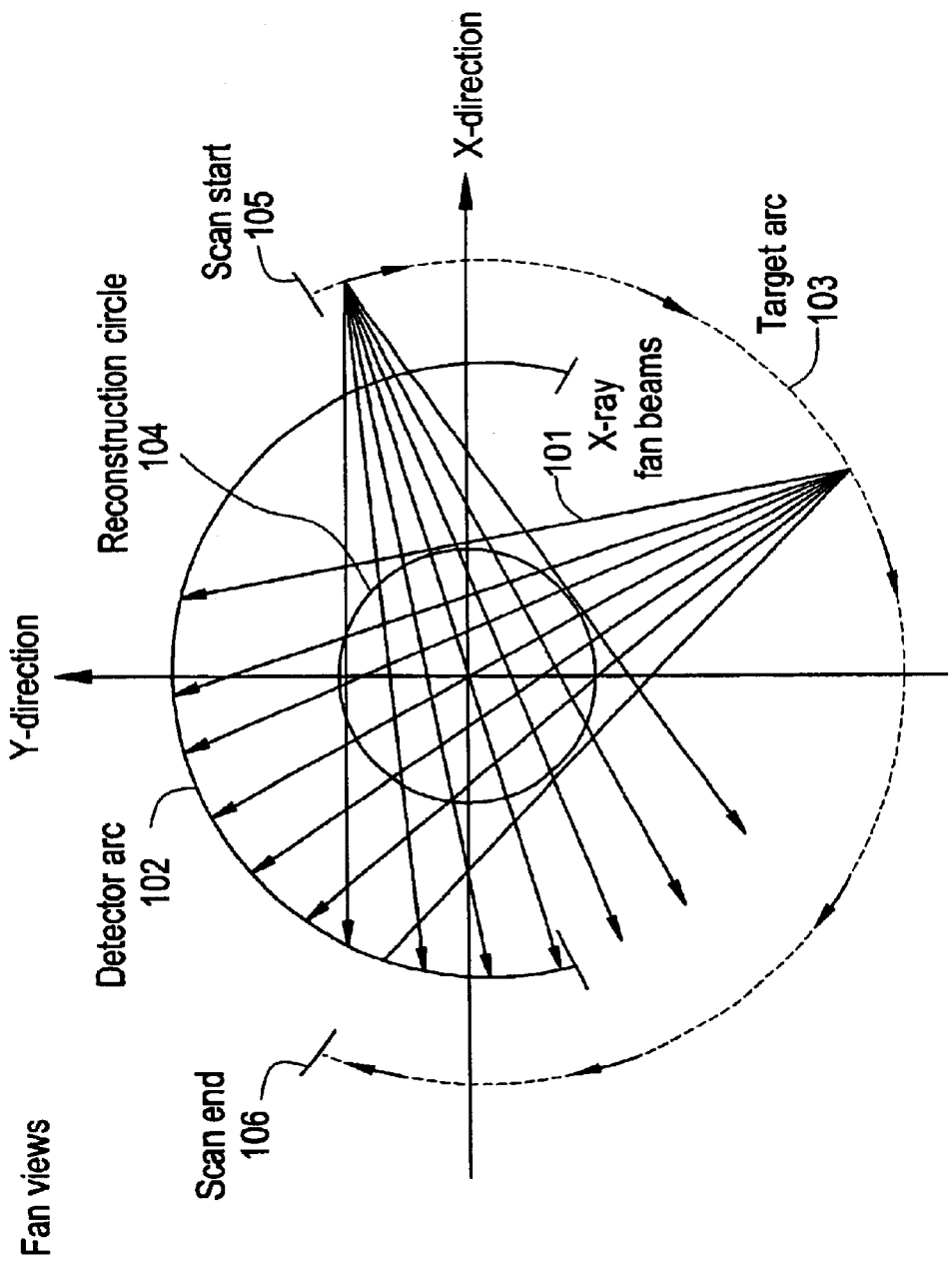
FIG. 3 is a conceptual representation of how scanning is performed over an angular field-of-view in an X-Y plane in accordance with an embodiment of the present invention.

FIG. 3 is a conceptual representation of how scanning is performed over an angular field-of-view of, for example, 210 degrees in an X-Y plane in accordance with an embodiment of the present invention. An X-ray fan beam 101 is rotated in the X-Y plane through various view angles as a subject is being scanned. Typically, the center of the fan beam is rotated through 210 degrees and detected by detector arc 102. The clockwise direction of rotation (scanning) is shown by the target arc 103.

Each fan beam position during scanning is referred to as a fan view angle. Each fan beam 101 from each fan view angle passes through a subject within the reconstruction circle 104 as scanning proceeds around the target arc 103. In an embodiment of the present invention, a single source fan beam has a fan width of 30.6 degrees.

At the beginning of a scan at scan start position 105, the fan beam 101 projects through the reconstruction circle 104 and impinges upon detector arc 102. However, part of fan beam 101 does not intersect the detector arc 102 as shown in FIG. 3. However, as the fan beam 101 rotates around the target arc 103, more and more of the fan beam 101 impinges upon the detector arc 102 until, at a certain angle, all of the fan beam 101 is intersected by the detector arc 102. Similarly, at the end of a scan at scan end position 106, not all of the fan beam 101 impinges upon detector arc 102.

All of the samples detected by a single detector element on the detector arc 102 over a single scan constitute a detector fan. All of the samples collected over a scan from all of the detector elements (all detector fans) constitute a fan view sinogram. In an embodiment of the present invention, there are 20 microseconds between X-ray fan beams 101 and there are 1728 detector elements distributed around the detector arc 102. Each detector fan comprises 864 data samples. Each complete scan around the target arc 103 takes 52 milliseconds with a 6 millisecond reset time before starting the next scan. Therefore, there is a temporal separation of 6 milliseconds between scans.

A total angular region greater than $\pi$ radians is covered in a single scan. Rays that are $\pi$ radians apart cover the same path through the object and are, therefore, redundant.

The redundant fan beam data may be used to effectively connect or feather temporally separated sinograms into each other. As a result, artifacts such as streaks may be eliminated in the final reconstructed image when imaging across temporal sinogram boundaries.

Figure 4:
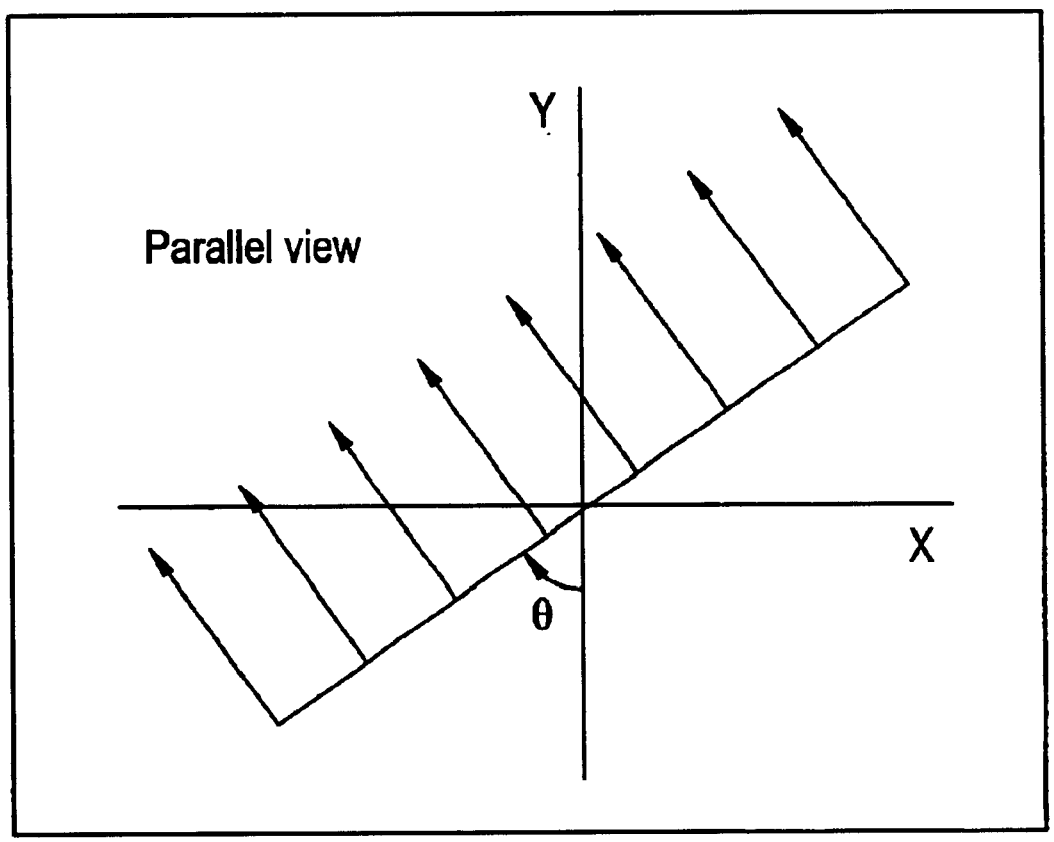
FIG. 4 is a conceptual illustration of a parallel view coordinate system in accordance with an embodiment of the present invention.

For efficient reconstruction of an image, it is preferable to translate the fan view sinogram to a parallel view sinogram. Then, an efficient reconstruction algorithm may be used on the parallel views during image reconstruction. The detector fan data may be translated to parallel views. A schematic of a parallel view is shown in FIG. 4 using the same coordinate system as in FIG. 3. The parallel view angle $\theta$ is referred to the negative Y-axis as shown.

The parallel views range in view angle between 39 degrees and 219 degrees in accordance with an embodiment of the present invention. Adjacent views are separated by ⅛ degree in view angle. Parallel views with view angles less than 0 degrees are redundant and may be folded or combined with the data for view angles less than 180 degrees. Similarly, parallel views with view angles greater than 180 degrees may be folded into the region with view angles greater than 0 degrees. However, in an embodiment of the present invention, the folding will be into temporally adjacent scans to allow imaging across temporal boundaries.

Figure 5:
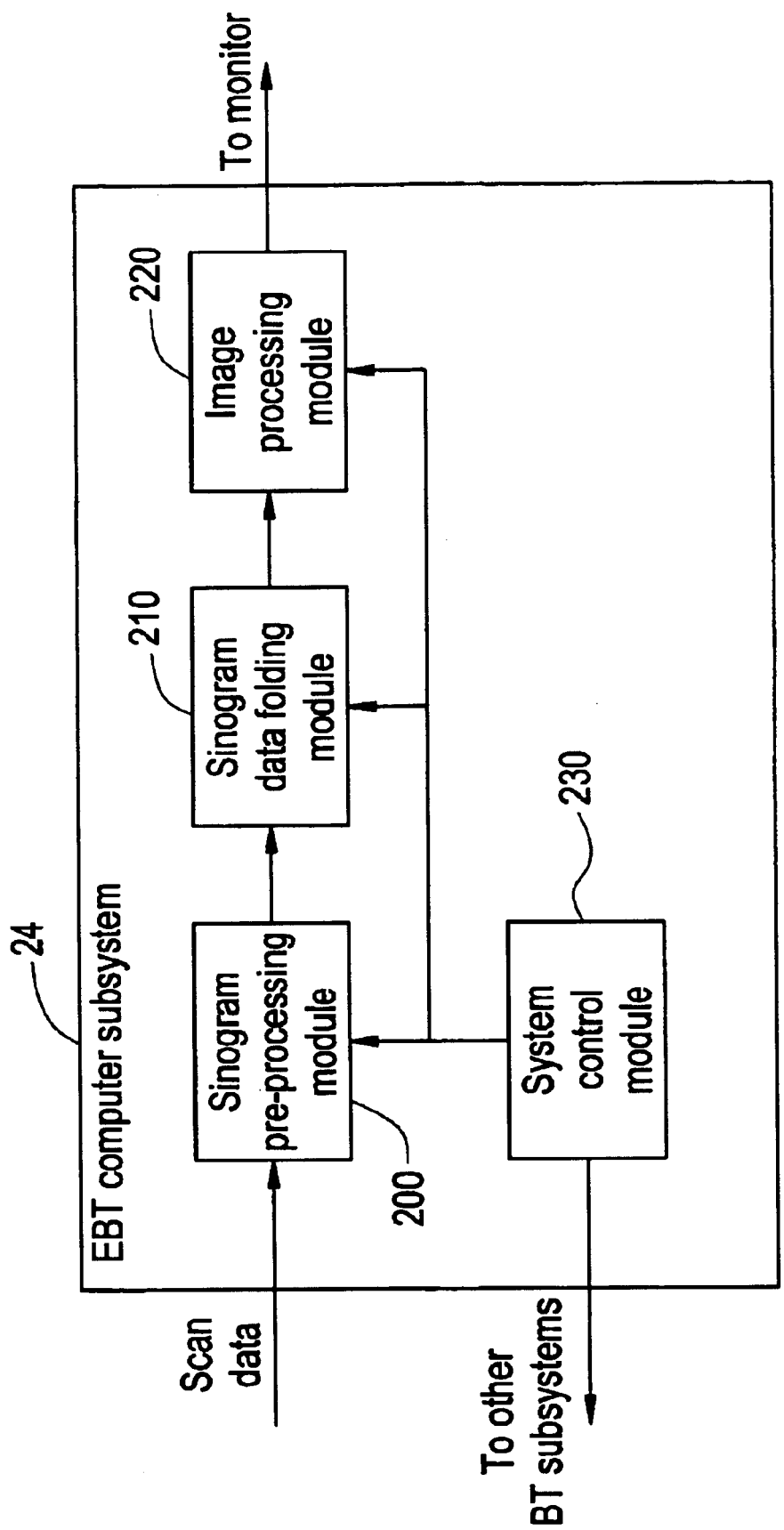
FIG. 5 is a schematic block diagram of at least a portion of an EBT computer subsystem within the EBT scanner of FIG. 1 and FIG. 2 in accordance with an embodiment of the present invention.

FIG. 5 shows at least a portion of the EBT computer subsystem 24 in accordance with an embodiment of the present invention. The EBT computer subsystem 24 comprises a sinogram pre-processing module 200, a sinogram data folding module 210, an image processing module 220, and a system control module 230.

Figure 6:
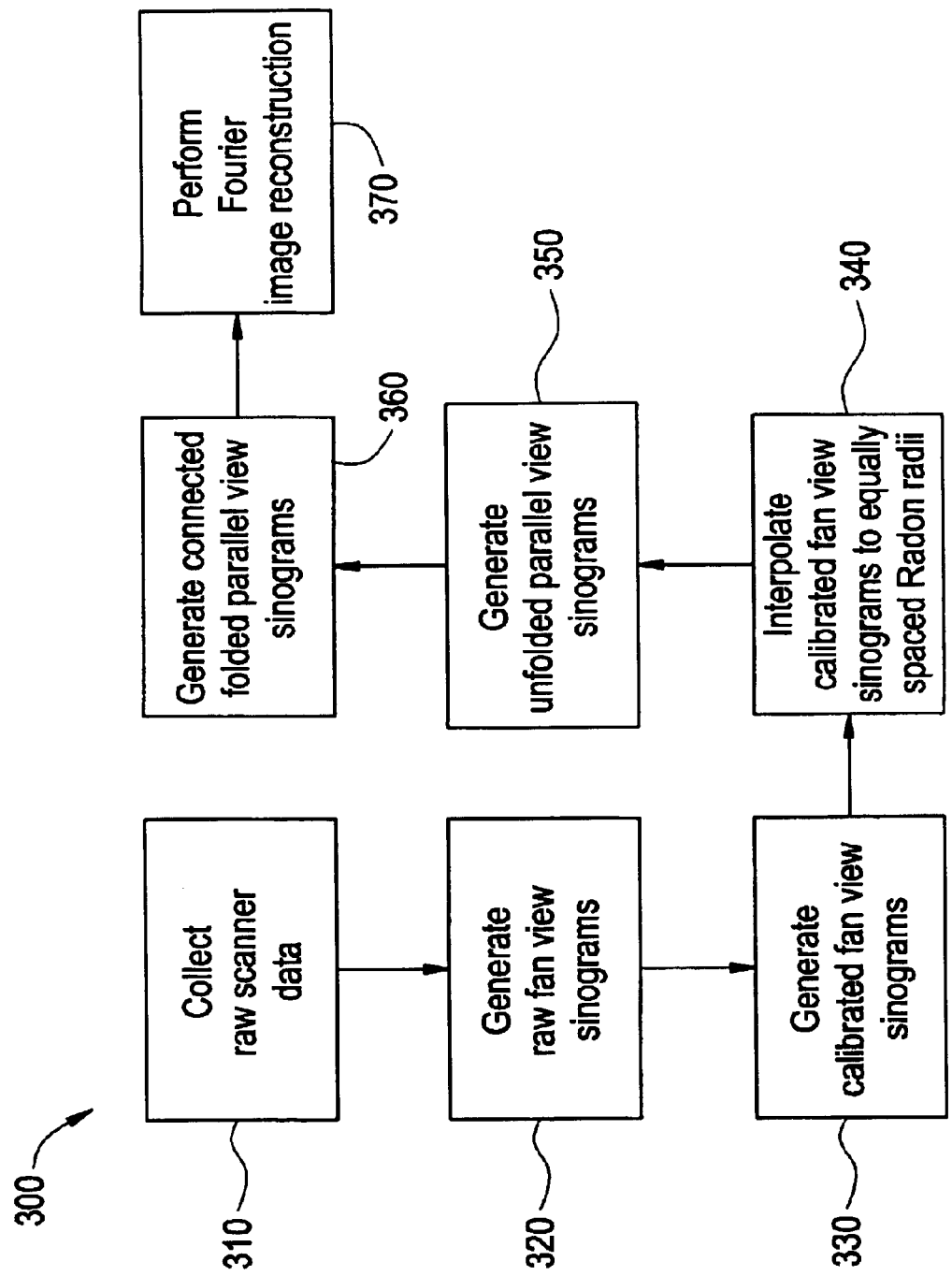
FIG. 6 illustrates a method to process and connect temporally separated sinograms in accordance with an embodiment of the present invention.

FIG. 6 illustrates a rebinning method 300 to process and connect the temporally separated sinograms in accordance with the present invention. In step 310, raw scanner data samples are collected during a scanning time interval. The raw scanner data samples are input to sinogram pre-processing module 200 in EBT computer subsystem 24. Sinogram pre-processing module 200 generates a raw fan view sinogram in step 320 for each scan within the scanning time interval and then calibrates the fan view sinograms in step 330. After calibration, the fan view sinograms are interpolated to equally spaced Radon radii in step 340. The Radon radius is the distance of closest approach that an X-ray path makes to the center of the reconstruction circle 104. By definition, equally spaced samples in a parallel view are equally spaced in Radon radii.

In step 350, the sinogram pre-processing module 200 translates the processed fan view sinograms to the parallel coordinate system. The translated sinograms are now unfolded parallel view sinograms. They are unfolded since the redundant rays have not yet been folded into the region $0<=\theta<=\pi$.

The rebinning process is used to interpolate the measured fan beam X-ray data to parallel views suitable for use by a Fourier reconstruction algorithm (step 370) in the image processing module 220 (see FIG. 5). As previously described, certain rebinning functions are performed by sinogram pre-processing module 200 in EBT computer subsystem 24 (see FIG. 5). The raw fan beam scan data enters sinogram pre-processing module 200 (step 310). After the detector fans have been calibrated, logged, and normalized to air, the samples are interpolated to equally spaced Radon radii (steps 320–340). During steps 320–340, the new fan view sinogram may be weighted to taper the corner edges and also to ensure that redundant rays that are 180 degrees apart are counted only once. Rays at large and small angles appear twice in the sinogram because the X-ray beam illuminates the subject from both sides.

The weighted, interpolated sinogram is then interpolated once more (or "rebinned") to parallel views (step 350) also by sinogram pre-processing module 200. Note that a given sample k refers to the same Radon radius s in both the interpolated detector fan sinogram and the parallel view sinogram. To obtain sample k for a parallel view, the two detector fans that contain sample k closest in angle to the parallel view angle are linearly interpolated to sample k in the parallel view. As a result, an "unfolded" parallel view sinogram that extends to view angles $\theta>\pi$ and $\theta<0$ is generated in step 350.

In an embodiment of the present invention, the final stage of the rebinning process is to fold samples from temporally adjacent unfolded parallel view sinograms into each other. In step 360, samples from the region $\theta>\pi$ of a given unfolded parallel view sinogram are folded into the region $\theta>0$ of a next temporally adjacent unfolded parallel view sinogram. Also, in step 360, samples from the region $\theta<0$ in a given unfolded parallel view sinogram are folded into the region $\theta<\pi$ of a previous temporally adjacent unfolded parallel view sinogram. The folding process uses the relation that $\theta$ goes to $\theta+\pi$ and s goes to s, where s is the Radon radius. In an embodiment of the present invention, folding is accomplished by sinogram data folding module 210 (see FIG. 5).

Figure 7:
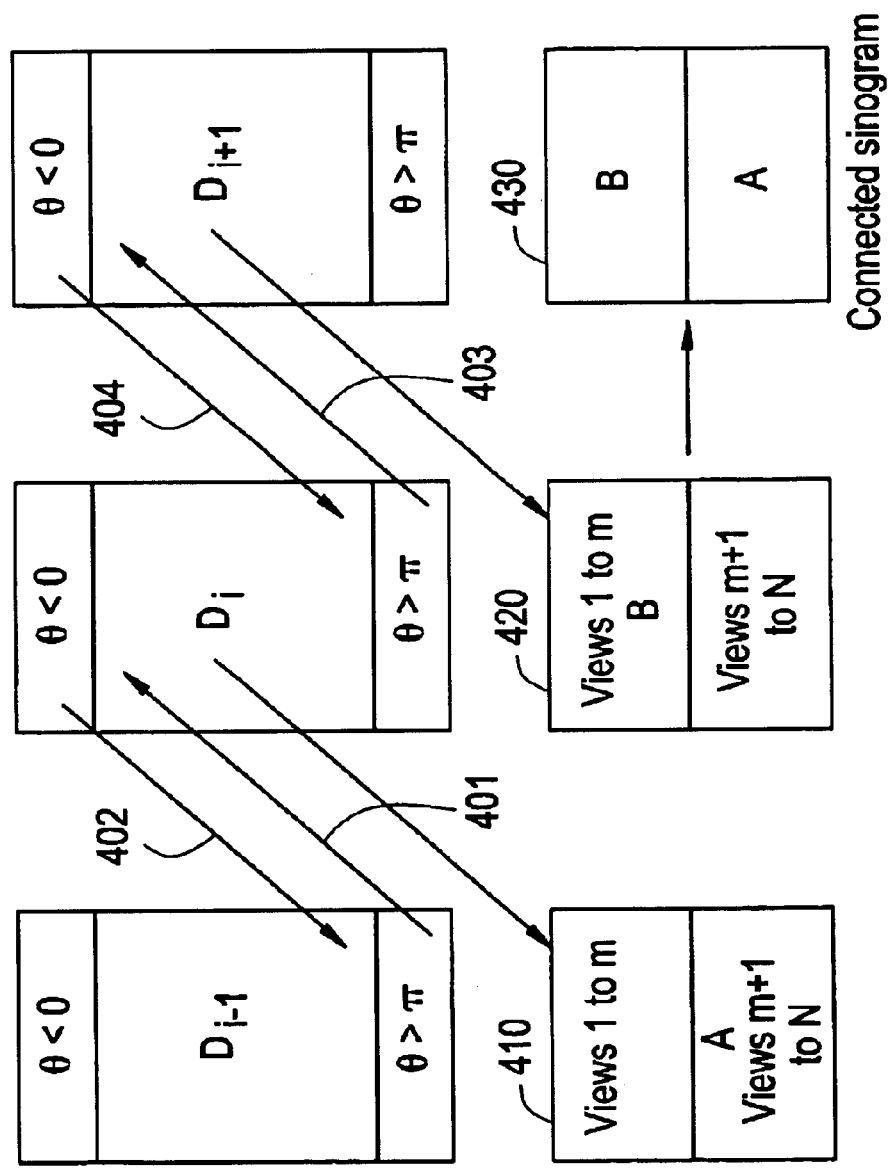
FIG. 7 is a conceptual illustration of how data from three temporally separated scans (sinograms) may be folded into each other in accordance with an embodiment of the present invention and how a data set may be selected beginning at an arbitrary time (view) within a scanning time interval to reconstruct an image in accordance with an embodiment of the present invention.

FIG. 7 is a conceptual illustration of how data from three temporally adjacent scans (unfolded parallel view sinograms) may be folded into each other in accordance with an embodiment of the present invention. Consider the three temporally separated (e.g. 6 millisecond gap) unfolded parallel view sinograms $D_{i-1}$, $D_i$, and $D_{i+1}$ shown in FIG. 7 and taken from somewhere within a scan sequence. Samples from the region $\theta>\pi$ in $D_{i-1}$ are folded into the region $\theta>0$ in $D_i$ step 360 as indicated by arrow 401, and samples from the region $\theta<0$ in $D_i$ are folded into the region $\theta<\pi$ in $D_{i-1}$ in step 360 as indicated by arrow 402. Also, samples from the region $\theta>\pi$ in $D_i$ are folded into the region $\theta>0$ in $D_{i+1}$ in step 360 as indicated by arrow 403, and samples from the region $\theta<0$ in $D_{i+1}$ are folded into the region $\theta<\pi$ in $D_i$ in step 360 as indicated by arrow 404.

In an embodiment of the present invention, folding is performed by weighting samples from a first and second region, summing the weighted samples to form folded samples, and replacing the samples in the second region with the folded samples.

For example, as previously described, data samples in the region 74 >$\pi$ are folded into the region $\theta>0$. A sample in the region $\theta>\pi$ may be weighted by a factor of, for example, 0.6 and the samples in the region $\theta>0$ may be weighted by a factor of 1−0.6=0.4 (notice that the weighting factors add up to one). Corresponding weighted samples (where $\theta$ goes to $\theta+\pi$ and s goes to s) are then summed together and the data samples in the region $\theta>0$ are replaced with the summed data samples.

As a result of the folding process, the temporally separated sinograms are made more temporally similar, allowing images to be reconstructed across the temporal boundaries without introducing artifacts.

Referring again to FIG. 7, it is desired to reconstruct an image from a time starting within a first sinogram 410 (e.g. $D_i$) and ending within a next temporally adjacent second sinogram 420 (e.g $D_{i+1}$) Each sinogram is made up of N folded parallel views. Views 1 to m (region B) are taken from the second sinogram 420 and views m+1 to N (region A) are taken from the first sinogram 410 to reconstruct a connected sinogram 430 comprising the views of region A and region B and also having a total of N views. Fourier image reconstruction is then performed on the new sinogram in step 370 by image processing module 220. The reconstructed image data is then presented on a monitor 26 for display to a user. By combining views from two temporally adjacent folded parallel view sinograms as just described, an artifact-free image that is not rotated may be generated.

The folding process may be performed for all boundaries across which at least one image is to be reconstructed for subsequent display and viewing.

As described, there are redundant rays near the beginning and end of the scan. Assume the table of the scanner is stationary but the object being scanned (such as the heart) is moving. Rays near θ=0 and rays near θ=π are separated by about 50 milliseconds. If the motion is fast enough in the Y direction (normal to the redundant rays), then motion artifacts may occur in the image because moving edges of the object are sampled 50 milliseconds apart at the beginning and end of the scan.

In accordance with an embodiment of the present invention, images are much less sensitive to motion in the X direction (along the rays). Moving edges are primarily sampled by rays along the +Y direction (θ=π/2), and all such rays in the image are much closer in time than 50 milliseconds because the edges are never sampled by rays from the opposite direction. Such observations have been verified by experiments with a motion phantom.

Now imagine that two sinograms are connected from two temporally adjacent heart scans (or phases) by combining the last half of the first sinogram with the first half of the last sinogram by using an embodiment of the present invention. Now the rays along the X direction are only about 6 milliseconds apart (the time between scans) rather than 50 milliseconds apart, however, rays along the +Y direction are separated by up to 50 milliseconds since the rays come from different scans. Hence, motion along the X direction yields artifacts but motion along the Y direction will tend to be free of artifacts. Such observations have also been verified by experiments with a motion phantom.

In general, artifacts that arise from motion that is predominantly along any direction may be minimized by choosing the correct view to begin the new sinogram. If a doctor is confused about whether a feature of an image is real or a motion artifact (a common clinical problem), the doctor may be provided with an application to select where the sinogram begins to attempt to eliminate any artifacts connected with the feature.

In an embodiment of the present invention, system control module 230 controls all of the system level functions of the EBT scanner including scanning.

The various modules of the EBT computer subsystem 8 may be combined or separated according to various embodiments of the present invention and may be various combinations of software and hardware modules according to various embodiments of the present invention. For example, sinogram pre-processing module 200 and sinogram data folding module 210 may be integrated into a single module. Also, the various modules 200, 210, 220, and 230, may be software modules running on a general purpose PC backend computer platform.

In summary, the advantages and features include, among others, an approach for eliminating the effects of temporal discontinuities between adjacent scans such as lost information or unwanted image artifacts in an EBT scanner. The data used to generate an image may be selected to begin at any point during the total scanning time and total distance scanned.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. In an electron beam tomography (EBT) scanner for scanning a subject during a scanning time interval, a method to generate an image from a data set collected from said subject beginning at an arbitrary time within said scanning time interval, said method comprising:

generating a sequence of temporally separated, unfolded parallel view sinograms corresponding to scans through said subject during a scanning time interval, wherein said sequence includes a first sinogram and a last sinogram, said first and last sinograms being temporarily adjacent;

folding data from a first region of view angles from each of said sinograms into a second region of view angles in a corresponding next temporally adjacent sinogram;

folding data from a third region of view angles from each of said sinograms into a fourth region of view angles in a corresponding previous temporally adjacent sinogram, wherein said folding data from said first region and said folding data from said third region include combining a last half of said first sinogram with a first half of said last sinogram; and generating an image from a subset of data taken from said sinograms wherein said subset of data begins at an arbitrary time within said scanning time interval.

2. The method of claim 1 wherein said folding comprises:

weighting a first set of data corresponding to one region of view angles of one sinogram and weighting a second set of data corresponding to a different region of view angles of a different corresponding temporally adjacent sinogram to form a first weighted set of data and a second weighted set of data;

summing together said first weighted set of data and said second weighted set of data to form a folded set of data; and replacing said second set of data with said folded set of data within said different region of view angles.

3. The method of claim 1 wherein said unfolded parallel view sinograms are generated from fan view sinograms.

4. The method of claim 1 wherein said generating an image includes applying a reconstruction algorithm to said subset of data.

5. The method of claim 1 wherein each of said sinograms is gathered over scanning view angles comprising at least a total of π radians.

6. The method of claim 1 wherein said first region of view angles comprises angles greater than π radians.

7. The method of claim 1 wherein said second region of view angles comprises angles greater than 0 radians.

8. The method of claim 1 wherein said third region of view angles comprises angles less than 0 radians.

9. The method of claim 1 wherein said fourth region of view angles comprises angles less than π radians.

10. The method of claim 1 further comprising selecting said arbitrary time within said scanning time interval to determine whether or not an imaged feature is an artifact.

11. The method of claim 1 wherein said method reduces motion artifacts within said image.

12. In an electron beam tomography (EBT) scanner for scanning a subject during a scanning time interval, apparatus to generate an image from a data set collected from said subject beginning at an arbitrary time within said scanning time interval, said apparatus comprising:

a sinogram pre-processing module generating a sequence of temporally separated, unfolded parallel view sinograms corresponding to scans through said subject during a scanning time interval, wherein said sequence includes a first sinogram and a last sinogram, said first and last sinograms being temporally adjacent;

a sinogram data folding module folding data from a first region of view angles from each of said sinograms into a second region of view angles in a corresponding next temporally adjacent sinogram, and said sinogram data folding module folding data from a third region of view angles from each of said sinograms into a fourth region of view angles in a corresponding previous temporally adjacent sinogram, wherein said sinogram data folding module combines a last half of said first sinogram with a first half of said last sinogram; and an image processing module generating image data from a subset of data taken from said sinograms wherein said subset of data begins at an arbitrary time within said scanning time interval.

13. The apparatus of claim 12 further comprising a monitor to display said image data as a video image.

14. The apparatus of claim 12 further comprising an electron gun in a vacuum chamber housing to generate an electron beam within said EBT scanner.

15. The apparatus of claim 12 further comprising at least one X-ray target to generate at least one fan beam of X-rays when impinged upon by an electron beam of said EBT scanner.

16. The apparatus of claim 12 further comprising a detector array to detect X-rays emitted by at least one X-ray target of said EBT scanner.

17. The apparatus of claim 12 further comprising a system control module to control various functions of said EBT scanner including scanning.

18. The apparatus of claim 12 wherein said first region of view angles comprises angles greater than $\pi$ radians.

19. The apparatus of claim 12 wherein said second region of view angles comprises angles greater than 0 radians.

20. The apparatus of claim 12 wherein said third region of view angles comprises angles less than 0 radians.

21. The apparatus of claim 12 wherein said fourth region of view angles comprises angles less than $\pi$ radians.

22. The apparatus of claim 12 wherein said apparatus reduces motion artifacts within said image.

* * * * *

UNITED STATES PATENT AND TRADEMARK OFFICE
CERTIFICATE OF CORRECTION

PATENT NO.    : 6,842,499 B2
DATED         : January 11, 2005
INVENTOR(S)   : Zapalac It is certified that error appears in the above-identified patent and that said Letters Patent is hereby corrected as shown below:

Column 8,
Lines 21-22, delete "temporarily" and substitute therefore -- temporally --.

Signed and Sealed this

Tenth Day of May, 2005

JON W. DUDAS
*Director of the United States Patent and Trademark Office*